United States Patent [19]

Ginsberg et al.

[11] Patent Number: 4,562,600
[45] Date of Patent: Jan. 7, 1986

[54] INTRAOCULAR LENS

[75] Inventors: Stephen P. Ginsberg, 9001 Potomac Station La., Potomac, Md. 20854; Durward I. Faries, Jr., McLean, Va.

[73] Assignee: Stephen P. Ginsberg, Potomac, Md.

[21] Appl. No.: 543,068

[22] Filed: Oct. 18, 1983

[51] Int. Cl.⁴ ............................ A61F 4/16; A61C 1/24
[52] U.S. Cl. ........................................................ 623/6
[58] Field of Search ........................................ 3/13, 1

[56] References Cited

U.S. PATENT DOCUMENTS

| | | | |
|---|---|---|---|
| 2,834,023 | 5/1958 | Lieb | 3/13 X |
| 3,866,249 | 2/1975 | Flom | 3/13 |
| 3,906,551 | 9/1975 | Otter | 3/13 |
| 3,913,148 | 10/1975 | Potthast | 3/13 |
| 3,925,825 | 12/1975 | Richards et al. | 3/13 |
| 3,971,073 | 7/1976 | Richards et al. | 3/13 |
| 3,994,027 | 11/1976 | Jensen et al. | 3/13 |
| 3,996,626 | 12/1976 | Richards et al. | 3/13 |
| 3,996,627 | 12/1976 | Deeg et al. | 3/13 |
| 4,073,014 | 2/1978 | Poler | 3/13 |
| 4,073,015 | 2/1978 | Peyman et al. | 3/13 |
| 4,080,709 | 3/1978 | Poler | 3/13 X |
| 4,110,848 | 9/1978 | Jensen | 3/13 |
| 4,118,808 | 10/1978 | Poler | 3/13 |
| 4,159,546 | 7/1979 | Shearing | 3/13 |
| 4,190,049 | 2/1980 | Hager et al. | 3/13 X |
| 4,198,714 | 4/1980 | Jensen | 3/13 |
| 4,244,060 | 1/1981 | Hoffer | 3/13 |
| 4,365,360 | 12/1982 | Ong | 3/13 |
| 4,412,359 | 11/1983 | Myers | 3/13 |
| 4,418,431 | 12/1983 | Feaster | 3/13 |

OTHER PUBLICATIONS

John H. Sheets, M.D., *Covered Bridge: An Update on Lens Implantation*, pp. 5-13 (1977).
"The Hoffer Ridged Optic", Iolab Corporation (1982).
"Laseridge", Iolab Corporation.
"The Hoffer Ridge Lenses from CILCO", Cilco, Inc. (Mar. 1983).
"The Model 150 Pearce Vaulted Y Posterior Chamber Lens", Coburn Optical Industries, Inc. (Apr. 1983).
"The New Clayman Lightweight", Precision-Cosmet Company, Inc. (1983).
"Ridged Intraocular Lens May Lower Need for Discissions After Cataract Extraction", *Ophthalmology Times*, vol. 6, No. 4 (Apr. 1981).
"Planned Extracapsular Catarac Extraction and the Insertion of the Lindstrom Centrex Style 20 Posterior Chamber Lens", by Richard L. Lindstrom, (Pamphlet), pp. 1-11, Copyright 1981.
Lins Implantation 30 Years of Progress, (Book), by P. Leonard et al, Dr. W. Junk Publishers, (Printed in Belgium), 1982, pp. 300-301.

(List continued on next page.)

*Primary Examiner*—Ronald L. Frinks
*Attorney, Agent, or Firm*—Robbins & Laramie

[57] ABSTRACT

An intraocular lens for implantation in the posterior chamber of a human eye following extracapsular cataract extraction comprises a lens body which includes a lens optic having a central axis, and a circumferential flange extending posteriorly and radially outward from the edge of the lens optic at an oblique angle with respect to the central axis of the lens optic. Resilient means are provided for supporting the lens body within the posterior chamber of the eye and for exerting posterior pressure on the lens body to urge the circumferential flange into contact with the posterior capsule. The angulated flange causes stretching or tenting of the posterior capsule with consequent reduction of capsular wrinkling, particularly in the central area of the capsule. The flange can be made flexible in order to produce further stretching and smoothing of the central posterior capsule. Additional advantages of the circumferential flange include reduction or elimination of epithelial cell migration and fiber growth toward the central posterior capsule, creation of a space between the lens and the capsular surface to allow laser capsulotomy procedures to be carried out without damage to the lens, and separation of the anterior capsule flap from the posterior capsule.

25 Claims, 17 Drawing Figures

OTHER PUBLICATIONS

Lester Posterior Chamber Lens, (Advertisement), Intermedics Intraocular Inc., P.O. Box 70670, Pasadena, CA 91107, (2 pages), Aug. 1982.

"Ovoid Optic Posterior Chamber Intraocular Lens: The First One Hundred Cases", by H. M. Clayman, Am. Intra-Ocular Implant Soc. J., vol. 8, Fall 1982, pp. 343–345.

Model PC-80 Posterior Chamber (Knolle) Intraocular Lenses, American Medical Optics, (Advertisement brochure), 4 pages, Sep. 1982.

The Hoffer Ridge Lenses from Cilco, (Advertisement brochure), Cilco, Inc., 1616 13th Ave., Box 1680, Huntington, West Virginia, 6 pages, Mar. 1983.

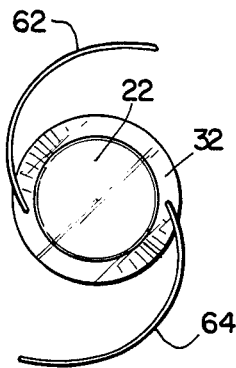
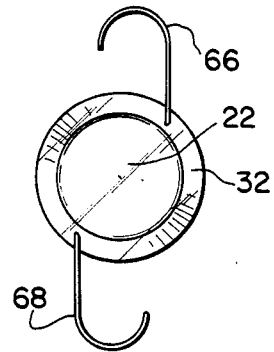
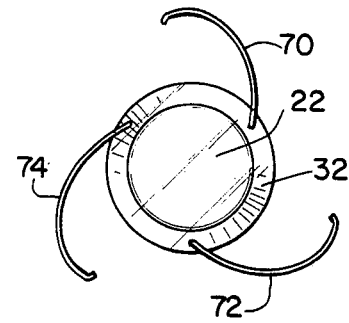
FIG. 12　　　FIG. 13　　　FIG. 14
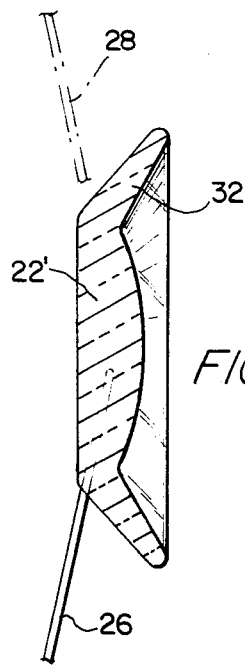
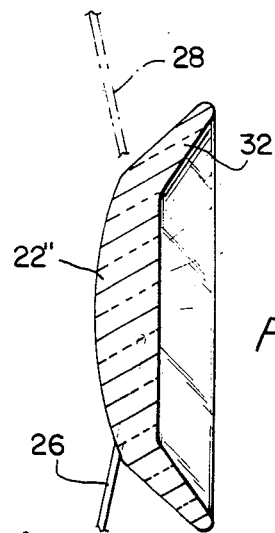
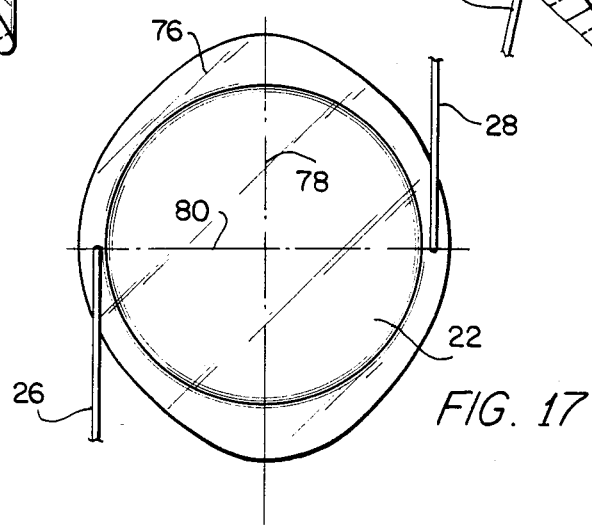
FIG. 15　　　FIG. 16　　　FIG. 17

INTRAOCULAR LENS

BACKGROUND OF THE INVENTION

1. Field of the Invention

The present invention relates generally to artificial lens implants for the human eye, and is particularly concerned with an intraocular lens for implantation in the posterior chamber of the eye following extracapsular cataract extraction.

2. Description of the Prior Art

A cataract is a condition in which the natural crystalline lens of the eye becomes partially or completely opaque. This can be a result of trauma, disease or of the natural aging process. Congenital cataracts also occur in some cases. Whatever the cause, the condition usually worsens over time, eventually reaching a point where vision is severely impaired. Special eyeglasses can be used to restore vision to some patients, but in many cases the cataract condition progresses to a point where surgery becomes necessary.

Cataract surgery involves the removal of the clouded natural lens, in whole or in part, followed by the substitution of some type of artificial lens. The artificial lens insures that light images are properly focussed on the retina in the absence of the natural lens. Before the development of implanted lenses, the artificial lens usually consisted of a corneal contact lens or aphakic eyeglasses. With aphakic eyeglasses, however, many patients experience undesirable side effects such as double vision, reduced side vision, and distortion of objects. Contact lenses eliminate some of these problems, but are difficult to handle and cannot be physically tolerated by some patients, particularly elderly patients. An additional problem with any type of external lens is, of course, that the patient is effectively left with no vision in the affected eye when the lens is removed.

This situation was greatly improved with the advent of the artificial intraocular lens (IOL). This type of lens is permanently implanted in the eye after cataract surgery to replace the natural crystalline lens. The implanted lens usually occupies a position within the eye that is relatively close to the position formerly occupied by the natural lens, and therefore serves as a nearly physiologic substitute with virtually no undesirable side effects on vision. A further advantage of this type of lens is that the patient is not faced with the difficulties involved in handling an external lens, or with the complete loss of vision that occurs when an external lens is removed. Of course, since the implanted IOL does not have the ability to focus by changing shape, as can the natural lens, patients receiving artificial lens implants may require eyeglasses for reading or distance. However, from the standpoint of a patient who has previously had a cataract, the occasional need for eyeglasses is usually considered to be a minor inconvenience.

Prior to the implantation of an artificial intraocular lens, a surgical procedure must be performed to remove the natural lens which contains the cataract. This may be done in one of two ways. In the procedure known as intracapsular cataract extraction (ICCE), the entire lens is removed including the surrounding capsule. The second procedure, known as extracapsular cataract extraction (ECCE), involves opening or excising the anterior capsule, and then removing the lens substance from the interior of the capsule. This is usually done in a piecemeal manner using either an ultrasonic phacoemulsification instrument or, more commonly, an irrigation-aspiration technique. The ECCE procedure leaves the posterior capsule in place, together with the zonular ligaments which join this membrane to the ciliary body. Generally, a portion of the anterior capsule in the form of an irregular annular flap is also left in place after ECCE. The annular cavity between the anterior capsule flap and the posterior capsule is referred to as the cleft or fornix of the capsule.

According to Dr. John H. Sheets, in the text entitled *Covered Bridge: An Update on Lens Implantation* (1977), the development of the intraocular lens can be traced back to 1949. Dr. Harold Ridley of Great Britain recognized that wartime pilots who had suffered eye injuries from the shattered plastic windshields of their aircraft had no adverse reaction to the plastic fragments embedded within the eye. This led Dr. Ridley to develop an artificial intraocular lens, made of a clear plastic material, that could be implanted in the posterior chamber of the eye following extracapsular cataract extraction. Unfortunately, implantation of the Ridley lens was followed by post-operative complications in a relatively high percentage of cases, sometimes requiring later removal of the implanted lens. Some of these problems were believed to be due to the size and weight of the lens, which were very great by modern standards. Post-operative clouding of the posterior capsule was also observed after implantation of the Ridley lens, a problem which still persists at the present time.

In part because of the problems experienced with early posterior chamber lens designs, many subsequent designs provided for implantation of the lens in the anterior chamber of the eye. These lenses were usually provided with peripheral supporting structures which could be placed within the angle at the intersection of the iris and the cornea. By virtue of their placement in the anterior chamber, which is more readily accessible to the surgeon, these lenses were somewhat easier to implant than the earlier posterior chamber lenses. Unfortunately, the angle fixation method used in most anterior chamber lens designs sometimes gave rise to problems such as iritis, glaucoma and corneal dystrophy.

The next step in the evolution of intraocular lens implants was the development of the iris fixation lens. This type of lens was secured to the iris by means of loops, clips, sutures or a combination of these. Iris fixation lenses were positioned either in the anterior chamber, in which case the lens was referred to as a prepupillary lens, or in the plane of the iris, in which case the lens was referred to as a pupillary or iris plane lens. In addition to avoiding many of the problems associated with angle fixation lenses, iris fixation lenses had the further advantage that the fixation method inherently resulted in the lens being properly centered with respect to the pupil. Iris fixation lenses, however, were not without their own problems. Principal among these were occasional subluxation or dislocation of the implanted lens, and possible interference with normal dilation and contraction of the iris.

Although many types of anterior chamber and iris fixation lenses are in use at the present time, there is an increasing preference for posterior chamber implantation as originally envisioned by Dr. Ridley. The posterior chamber is the location of the natural crystalline lens before its removal, and for that reason, it is generally considered to be the most appropriate location for a truly physiologic lens implant. A typical present-day posterior chamber lens design, based on a much earlier anterior chamber lens developed by Barraquer, consists of a lens body supported by at least two curved strands or loops of resilient material extending outwardly from the edge of the lens body. U.S. Pat. No. 4,159,546, to Steven P. Shearing, describes a lens of this type and a method for implanting the lens in the posterior chamber following intracapsular or extracapsular cataract extraction. The implantation method involves placing the curved ends of the resilient loops against the ciliary body in the groove or sulcus immediately behind the iris. The spring-like resilience of the loops provides proper centering and fixation of the lens within the posterior chamber. In cases where the lens is implanted following extracapsular extraction (ECCE), the posterior lens surface can be further supported by the posterior capsule to achieve capsular fixation. Currently available versions of the Shearing lens include one type in which the resilient loops are made slightly shorter to allow them to be placed within the cleft or fornix of the capsular remnant, rather than in the ciliary sulcus.

At the present time, ECCE is the preferred technique of cataract extraction since it leaves the posterior capsule in place and thereby maintains the physiologic barrier between the posterior chamber and the vitreous body. The maintenance of this barrier is believed to eliminate or at least reduce a number of post-operative complications, particularly cystoid maculopathy, retinal detachment, and vitritis. Unfortunately, with the posterior capsule left in place, it frequently happens that residual epithelial cells proliferate and migrate from the equatorial region of the capsule toward the center, causing gradual clouding of the capsule and eventually impairing vision. The continued proliferation of these live cells results in the formation of cellular deposits which are known as Elschnig's pearls. Fibrous scar tissue also forms on the posterior capsule in many cases. Scraping or polishing of the posterior capsule is usually performed during the initial ECCE procedure to remove any cellular debris, but it is nearly impossible to remove all of this material.

Post-operative clouding of the posterior capsule has usually been remedied in one of two ways, both involving minor follow-up surgery. In the first method, a cutting or discission of the central posterior capsule is performed in order to allow light to pass through the clouded capsule to the retina. The second method involves repolishing or scratching the posterior capsule to eliminate the clouding condition. The problem with this approach, however, is that the clouding condition can reappear fairly rapidly unless the posterior capsule has been carefully scraped out to its peripheral edge. Regardless of which method is chosen, additional difficulties are presented when a posterior chamber lens implant is already in place, since it is then necessary to manipulate the discission knife or scratching instrument behind the lens.

There has been at least one attempt to design a posterior chamber lens implant which would eliminate clouding of the posterior capsule due to epithelial cell migration and fiber growth. U.S. Pat. No. 4,244,060, to Kenneth J. Hoffer, describes a posterior chamber lens which incorporates an annular ridge or lip projecting directly rearward from the central optical region of the lens body. The ridge or lip is intended to seat against the posterior capsule when the lens is implanted after extracapsular cataract extraction, thereby providing a barrier to inhibit the expansion of lens fibers or Elschnig's pearls into the central region of the capsule. Sections are left missing from the annular ridge to allow a discission knife to be inserted into the space behind the lens. In this way, a knife discission can be performed without dislodging the lens in the event that clouding of the posterior capsule occurs despite the barrier. A second function of the annular ridge or lip is to serve as a barrier for preventing vitreous material from coming forward into the anterior chamber after a discission has been done. Modified versions of the Hoffer lens are being sold at the present time, and, while some decrease in the discission rate has been reported for patients receiving this lens, there has been no conclusive proof that the ridge has a definite effect in lowering the need for discission.

A recent and important advance in the field of ophthalmology has been the use of the neodymium-YAG laser to treat clouding of the posterior capsule following extracapsular cataract extraction. The laser is simply focussed in the vicinity of the posterior capsule from a point outside the eye, and is then pulsed repeatedly until enough of the capsule is destroyed to remove the clouding condition and thereby improve vision. With the advent of the YAG laser, a condition that had previouly required follow-up surgery could now be remedied by means of a fairly simple and non-invasive office procedure. One problem that remained, however, was the potential for damage to an implanted posterior chamber lens during the laser capsulotomy procedure, particularly in cases where the lens was positioned very close to, or in contact with, the posterior capsule. In these situations, the repeated laser firings can cause undesirable pitting and cracking of the lens implant. One solution to this problem is to provide a spacing between the posterior capsule and the rear face of the lens, so that the YAG laser can be focussed in the vicinity of the capsule without damaging the posterior lens surface. The modified versions of the Hoffer lens, referred to previously, make use of this principle by employing the annular ridge or lip to separate the rear face of the lens from the posterior capsule.

Although the use of the YAG laser for posterior capsulotomies has greatly alleviated the problems attending extracapsular cataract extraction and posterior chamber lens implantation, the fact still remains that patients receiving lens implants after ECCE cannot be assured of a good result without accepting the possibility that follow-up procedures may be required to open the posterior capsule in the event that clouding occurs. In addition to clouding due to epithelial cell migration or fiber growth, other undesirable conditions affecting the posterior capsule may occur after the initial surgery. For example, it sometimes happens that large residual tags of anterior capsule are left after the anterior capsule is opened during ECCE. After surgery, these tags can become adherent to the posterior capsule, inducing fibrotic activity at their contact points. The annular pattern of scar tissue that often results from this condition is referred to as a Sommering ring. The fibrotic tissue can contract and distort the central posterior capsule, resulting in fine wrinkling of the posterior capsule behind the lens implant. This condition is believed to be responsible for the double and triple ghost images that some patients experience after implant surgery.

Either of the two conditions mentioned previously, capsular wrinkling or capsular clouding due to epithelial cell migration and fiber growth, can require a posterior capsulotomy which would not otherwise have been required. Currently available posterior chamber lens designs have not addressed these problems. While it is true that the YAG laser is useful in these situations, the laser capsulotomy procedure still has the disadvantage that it breaks the natural barrier between the aqueous and vitreous, and hence increases the risk of cystoid maculopathy, retinal detachment, and vitritis. In addition, the long term effects of the YAG laser on the eye are not known at this time.

Rather than relying on corrective follow-up procedures to open the posterior capsule after the onset capsular clouding or wrinkling, it would be far more desirable to prevent the occurrence of these conditions in the first place by appropriate design of the lens implant. In this way, the posterior capsule may be left intact and the patient may be spared the necessity of undergoing follow-up procedures after the initial implant surgery. This objective has unfortunately not been met by prior art designs for posterior chamber lens implants.

SUMMARY OF THE INVENTION

In accordance with the present invention, the foregoing disadvantages and limitations of the prior art are substantially avoided by providing an improved intraocular lens for implantation in the posterior chamber of a human eye following extracapsular cataract extraction. The intraocular lens comprises a lens body which includes an inner lens optic having a central axis and a circumferential flange extending posteriorly and radially outward from the edge of the lens optic at an oblique angle relative to the central axis of the lens optic. Resilient means are provided for supporting the lens body within the posterior chamber of the eye, and for exerting posterior pressure on the lens body to urge the circumferential flange into contact with the posterior capsule. Preferably, the circumferential flange is formed integrally with the lens optic, and extends posteriorly from the lens optic by a sufficient distance to create a space between the rear face of the lens optic and the posterior capsule.

As a result of the angulated circumferential flange extending from the edge of the lens optic, the rearward pressure exerted by the resilient supporting means is concentrated along a narrow line of contact with the posterior capsule. This results in a tenting or stretching of the posterior capsule, which in turn produces a smoothing effect that is particularly pronounced in the central region of the capsule beneath the lens optic. The central posterior capsule is thereby rendered smooth and substantially free of wrinkles. Post-operative wrinkling of the posterior capsule frequently occurs after posterior chamber lens implantation, and this condition is believed to be responsible for the double and triple ghost images that some patients experience after implant surgery. The present invention substantially avoids this result by eliminating or at least minimizing wrinkle formation in the central portion of the posterior capsule.

In a particularly preferred embodiment of the present invention, the angulated circumferential flange is adapted to flex slightly relative to the lens optic as the flange is urged into contact with the posterior capsule by the resilient supporting means. The flexing of the circumferential flange occurs in a generally radial direction away from the central axis of the lens optic, and thereby exerts a further stretching and smoothing effect which is concentrated on the central portion of the posterior capsule. This is highly advantageous from the standpoint of avoiding wrinkle formation in the central posterior capsule after the lens has been implanted.

The present invention provides for increased pressure of the lens body in the direction of the posterior capsule, to insure that the peripheral flange seats firmly and securely against the surface of the posterior capsule. This result is obtained by an impovement in the resilient supporting means, in particular, by the use of resilient supporting strands or loops which are provided with a greater amount of anterior tilt or inclination than has previously been thought necessary. As a consequence of the increased pressure of the flange against the posterior capsule, the capsule stretching effect is enhanced, and the possibility of post-operative wrinkling of the posterior capsule is further reduced.

The circumferential flange of the present invention has several additional advantages which are highly desirable from the standpoint of minimizing post-operative complications. In the first place, the flange produces a vaulting of the lens with respect to the posterior capsule, resulting in a space between the rear face of the lens optic and the surface of the posterior capsule. Due to the capsule stretching and smoothing effect of the flange as discussed previously, loose folds or wrinkles are not likely to appear in the central region of the posterior capsule, and hence there is very little chance that any part of the central posterior capsule will touch or closely approach the rear face of the lens optic. Consequently, in the event of post-operative clouding of the posterior capsule due to epithelial cell migration or some other cause, a laser capsulotomy procedure can easily and safely be carried out on the posterior capsule without the risk of damage to the lens implant. However, unlike prior art lens designs in which an annular ridge or lip extends perpendicularly from the rear face of the lens, the angulated peripheral flange used in the present invention actually extends beyond the edge of the lens optic in the radial direction. As a result, the clearance between the rear face of the lens optic and the posterior capsule extends across the entire diameter of the lens, allowing the laser to be focussed virtually anywhere behind the lens without causing damage. The circumferential location of the flange also allows better visualization of the peripheral retina by the surgeon, so that pathology in that area can be discovered more easily by visual examination.

A further advantage of the present invention is that the circumferential flange serves as a barrier for retarding or perhaps even eliminating epithelial cell migration and fiber growth toward the central portion of the posterior capsule. The rearward or posterior pressure exerted by the resilient supporting means is concentrated along a narrow line of contact between the circumferential flange and the posterior capsule, resulting in an efficient barrier between the equatorial and central regions of the posterior capsule. The increased anterior tilt of the resilient strands or loops which serve as the resilient supporting means increases the amount of this pressure and hence enhances the barrier effect of the flange. Therefore, by virtue of the peripheral flange, coupled with the increase rearward pressure exerted by the resilient supporting means, the likelihood of post-operative clouding of the posterior capsule is reduced with the present invention.

Importantly, the placement of the flange at the very edge of the lens, coupled with the outward angulation of the flange, results in an epithelial migration barrier located relatively far out to the margin of the posterior capsule. As a result, a larger area of the central posterior capsule is protected from epithelial cell migration than would be possible using the prior art approach, in which the barrier function was produced by a simple annular ridge or lip extending directly rearward from the rear face of the lens.

An additional advantage of the present invention lies in the fact that the angulation of the circumferential flange allows it to be interposed between the posterior capsule and the anterior capsule flap or remnant that results from the opening of the anterior capsule during ECCE. This insures 360° separation of the anterior capsular flap from the posterior capsule and consequently reduces the amount of fibrosis and contraction (i.e., pulling on the capsule) that is induced by capsular touching. At the same time, Sommering ring formation is either eliminated or located so far peripherally that it does not interfere with vision or with subsequent evaluation of the peripheral retina. This result is not obtainable with prior art barrier lens designs employing a simple annular ridge or lip extending perpendicularly from the rear face of the lens.

In some cases it may be necessary to implant the lens of the present invention in a manner such that the flange is in contact with the anterior capsule flap rather than with the posterior capsule directly. In these cases, a so-called "capsular seal" is created when the anterior capsule flap becomes adherent to the surface of the posterior capsule. The present invention is particularly useful in this situation since the concentration of rearward pressure on the circumferential flange presses the anterior capsule flap firmly into contact with the posterior capsule, thereby promoting the formation of the capsular seal. In addition, the angulation of the flange causes the capsular seal to be formed far out to the margin of the posterior capsule, thereby reducing the possibility that fibrosis may induce wrinkling of the central posterior capsule.

Additional aspects of the present invention include the provision of an intraocular lens with one or more open notches formed along the periphery of the lens body in lieu of, or in addition to, the round positioning holes employed in the prior art; the provision of an intraocular lens in which the lens body is supported by resilient upper and lower supporting strands or loops, the upper or superior loop being provided with a notch pointing downward in the direction of the lens body to facilitate insertion of the lens into the eye; and the provision of an intraocular lens with a non-circular haptic rim to allow the lens to be inserted into the eye through a smaller corneal incision than would otherwise be required.

BRIEF DESCRIPTION OF THE DRAWINGS

The various objects, advantages and novel features of the present invention will be more readily apprehended from the following detailed description when read in connection with the appended drawings, in which:

FIGS. 12-14 illustrate alternative types of supporting loops for the lens of FIG. 1, including one embodiment in which three loops are employed;

FIG. 15 illustrates a modified embodiment in which the lens optic has a plano-convex shape, with the plane surface being provided on the front face of the lens optic;

FIG. 16 illustrates a further modified embodiment in which the lens optic has a convex-plano shape, with the plane surface being provided on the rear face of the lens optic; and FIG. 17 illustrates a still further embodiment in which the outer haptic rim of the lens is elliptical in shape to facilitate insertion of the lens into the eye through a small corneal incision.

Throughout the drawings, like reference numerals are used to identify like parts.

DETAILED DESCRIPTION OF THE PREFERRED EMBODIMENTS

Figure 1:
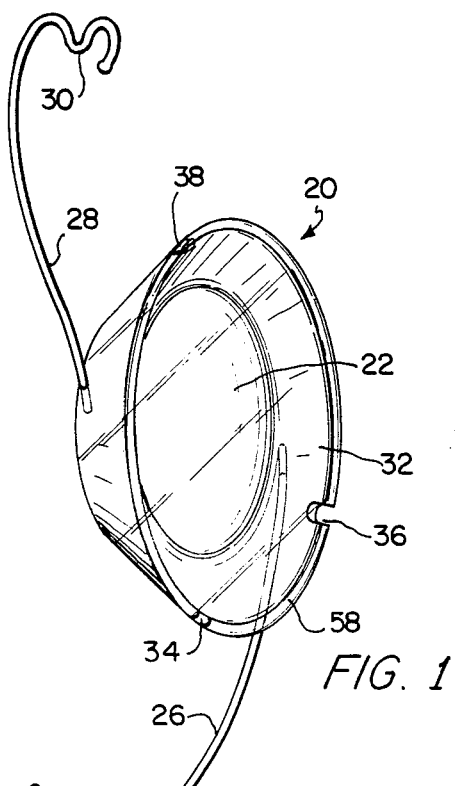
FIG. 1 is a rear perspective view of a biconvex posterior chamber intraocular lens constructed in accordance with the present invention, illustrating the circumferential flange which extends posteriorly and radially outward from the edge of the lens optic.

A posterior chamber intraocular lens constructed in accordance with the principles of the present invention is illustrated in FIGS. 1-5. The lens structure includes a transparent plastic lens body 20, the latter comprising an inner lens optic 22 and an outer haptic rim 32. In the illustrated embodiment, the lens optic 22 has a biconvex shape in cross-section, as will be evident from FIG. 5. An imaginary central or optical axis 24 passes longitudinally through the lens optic 22 as shown in FIGS. 2-5.

In accordance with an important feature of the present invention, the haptic rim 32 is provided in the form of a circumferential flange 32 extending posteriorly (i.e., rearwardly) and radially outward from the edge of the lens optic 22 at an oblique angle relative to the central or optical axis 24. The flange 32 extends completely around the circumference of the lens optic 22 as shown. In the illustrated embodiment, the angle of the flange 32 with respect to the axis 24 is indicated at a in FIG. 5. The angle a is preferably in the range between 30° and 38°, although different angles may be employed without departing from the scope of the invention. When the lens 20 is in position within the posterior chamber of the eye (not shown in FIGS. 1-5), the flange 32 is urged into contact with the posterior capsule that remains after extracapsular cataract extraction. The flange 32 is preferably formed integrally with the lens optic 22, as shown, and extends posteriorly from the lens optic by a sufficient distance to create a space between the rear face of the lens optic and the posterior capsule. This space, which is indicated at b in FIG. 5, corresponds to the gap between the rear face of the lens optic and the rearmost extent of the flange 32 at its outer periphery.

The lens body 20 is supported and centered within the posterior chamber of the eye (not shown) by means of upper and lower curved strands of resilient material, which are indicated by the reference numerals 28 and 26, respectively. The strands 26 and 28 extend outwardly from the flange 32, as shown, with each strand having one end secured to the flange and the other end free. When two strands are employed, as in the illustrated embodiment, they are preferably secured at diametrically opposed points along the periphery of the flange 32. It should be appreciated that, in some embodiments of the invention, it may be possible to secure the strands 26 and 28 directly to the lens optic 22 rather than to the outer flange 32.

Figure 2:
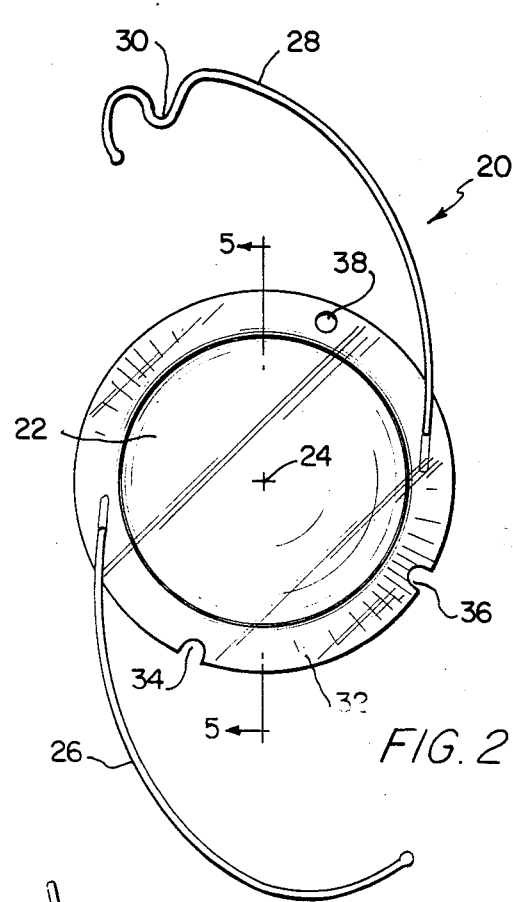
FIG. 2 is a front elevational view of the lens shown in FIG. 1, illustrating the configuration of the two flexible supporting loops and the novel positioning notches formed along the upper periphery of the lens body.
Figure 3:
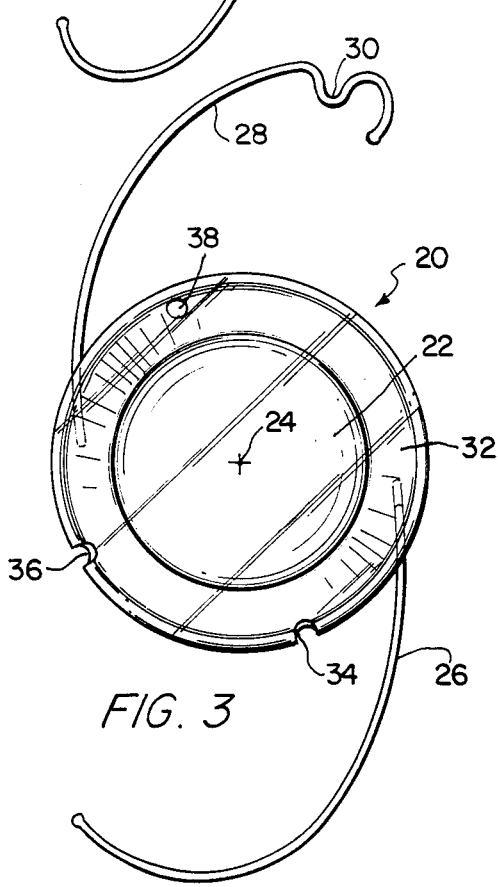
FIG. 3 is a rear elevational view of the lens shown in FIG. 1, also illustrating the loop configuration and the positioning notches.

The strands 26 and 28 are usually referred to as loops by ophthalmic implant surgeons, and that term will be employed hereinafter. The upper loop 28 is referred to as the superior loop, while the lower loop 26 is referred to as the inferior loop. As shown in FIGS. 1–3, the superior loop 28 is formed with a notch 30 for a purpose to be described shortly.

Figure 4:
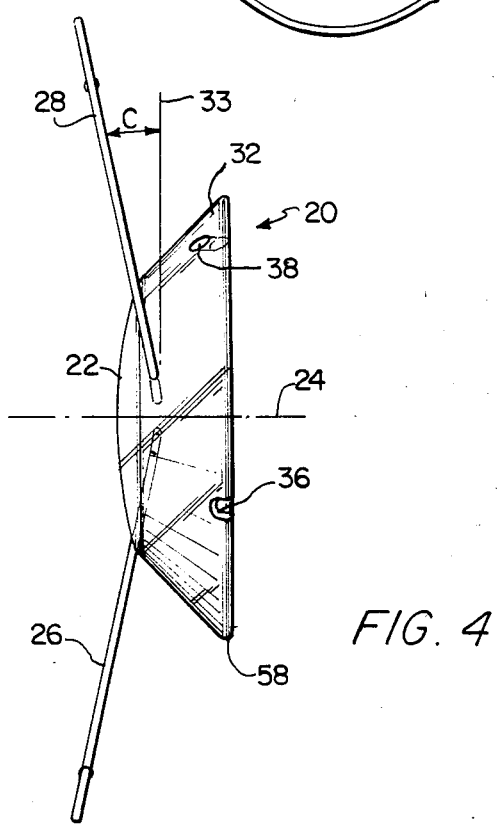
FIG. 4 is a side view of the lens shown in FIG. 1, illustrating the anterior tilt of the supporting loops.
Figure 5:
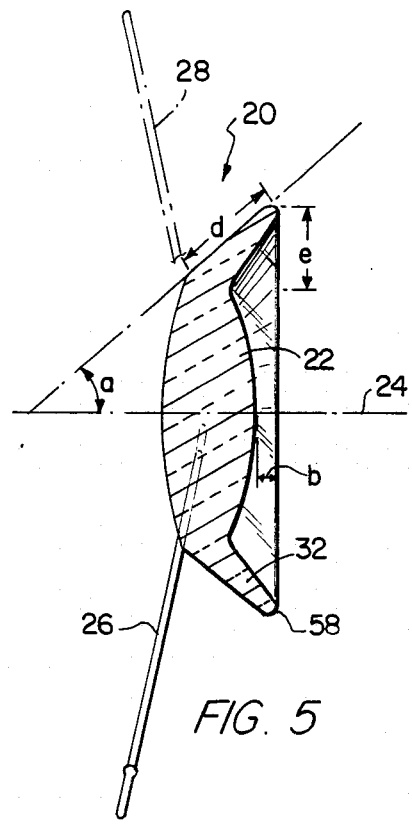
FIG. 5 is a side cross-sectional view of the lens taken along the line 5—5 in FIG. 2.

As best seen in FIGS. 4 and 5, the inferior and superior loops 26 and 28 lie in planes that are inclined anteriorly with respect to an imaginary reference plane 33 (seen edge-on in FIG. 4) lying normal to the central axis 24 of the lens optic 22. The angle of inclination, indicated at c in FIG. 4, is preferably greater than about 10° and is optimally chosen to be about 15°. This is somewhat greater than the 10° to 12° loop angulation currently used with other types of posterior chamber lenses. The purpose of the increased anterior tilt of the loops 26 and 28 in the present invention is to cause the flange 32 to exert an increased pressure on the posterior capsule of the eye after implantation, as will be discussed further in connection with FIG. 6.

With particular reference to FIGS. 1–3, the lens body 20 is provided with open semicircular notches 34 and 36 formed at spaced points along the rearmost outer periphery of the circumferential flange 32. The purpose of the notches 34 and 36 is to allow rotational positioning of the lens body 20 during the initial implant surgery. The surgeon may accomplish this by inserting a hook into one of the notches 34 or 36, and then rotating the lens body 20 to the desired position. In the past, round holes have been provided near the periphery of the lens for this purpose. In some cases, however, patients have experienced annoying flashes of light in the visual field, caused by reflections from the edges of the positioning holes. These reflections usually occur when the lens becomes slightly de-centered after implantation, so that the positioning holes are no longer covered by the iris and are closer to the optical axis. The use of open notches, rather than round holes, renders this phenomenon less likely since the notches are necessarily placed at the outermost perimeter of the lens, and hence are located farther from the optical axis 24 than would be the case for round holes of comparable diameter. In the illustrated embodiment, the spacing between the notches 34, 36 and the optical axis 24 is further enhanced by the fact that the notches are formed in the peripheral flange 32 of the lens body 20 rather than in the lens optic 22.

It is also possible to provide the lens body 20 with one or more conventional positioning holes 38, as shown, in addition to the notches 34 and 36. The positioning holes may be provided either in the circumferential flange 32, as in the illustrated embodiment, or in the lens optic 22. Placement of the positioning holes in the flange 32 is preferred because this results in a greater distance between the holes and the optical axis 24 of the lens optic, thereby reducing undesirable reflections from the hole edges as discussed earlier. It should be appreciated that, by virtue of the additional radial size of the lens body 20 attributable to the angulated flange 32, the present invention assists in the reduction of these unwanted reflections even when conventional positioning holes 38 are formed in the flange in lieu of the notches 34 and 36. An additional advantage is that the ovoid shape of the hole opening on the anterior surface of the flange 32 (best seen in FIG. 4) tends to cause any reflections to be directed peripherally rather than toward the visual axis.

Figure 6:
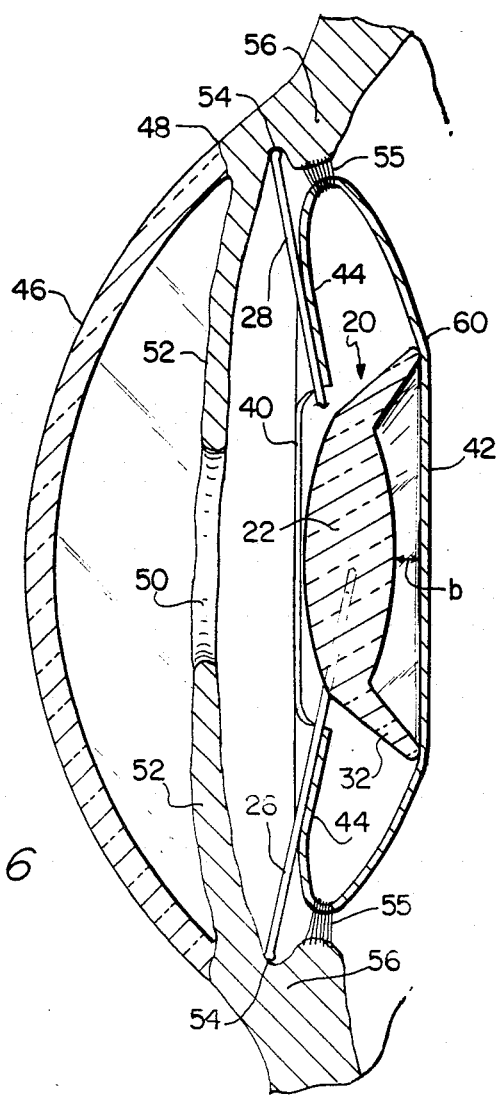
FIG. 6 is a sectional view through the forward part of the human eye, illustrating the lens of FIG. 1 implanted within the posterior chamber following extracapsular cataract extraction.

FIG. 6 illustrates the intraocular lens of FIGS. 1–5 after it has been implanted within the posterior chamber of the human eye following extracapsular cataract extraction. The ECCE procedure is carried out in the usual manner, beginning with an anterior capsulotomy to produce an opening 40 of about 7.5 to 8.0 millimeters in diameter in the anterior capsule. Since the preferred outer diameter of the lens body 20 is about 7.2 millimeters, an opening of the size indicated will insure that the edge of the flange 32 will be in direct contact with the posterior capsule 40 after implantation. If the anterior capsule opening is less than 7.2 millimeters in diameter, care must be taken to place the flange 32 in 360° contact with the posterior capsule 42 by slipping the flange below the anterior capsule flap 44.

The anterior capsulotomy is preferably accomplished using the so-called "can opener" technique, in which a bent needle is used to make small triangular tears along the desired line of excision. Following the anterior capsulotomy, the lens substance is removed either by an irrigation-aspiration technique or with an ultrasonic phacoemulsification instrument. All that remains of the natural lens when this procedure is complete is the posterior capsule 42 and the annular flap 44 of the anterior capsule.

After the lens material has been removed, the intraocular lens may be implanted in the posterior chamber in the usual manner through a limbal incision formed at the margin of the cornea 46. The preferred location of this incision is indicated by the reference numeral 48 in FIG. 6. The inferior loop 26 is passed through the incision and then through the dilated pupillary opening 50, eventually reaching the space behind the iris 52. The inferior loop 26 is then manipulated so that it rests against the ciliary body 56 in the groove or sulcus 54 located immediately behind the iris 52. At this stage the lens body 20 has moved through the pupil 50 and into the posterior chamber, although the superior loop 28 is still located forward of the iris 52. The procedure is completed by exerting downward pressure on the superior loop 28 in the direction of the inferior loop 26, causing the latter to compress sufficiently to allow the superior loop to move past the edge of the pupillary opening 50. The superior loop 28 may now be released so that it may seat against the ciliary sulcus 54, and as this occurs the inferior loop 26 is released somewhat from its compressed state. When the implantation is complete, the lens body 20 is centered within the posterior chamber by virtue of the balancing forces exerted on the lens body by the resilient loops 26 and 28.

The function of the notch 30 which is formed in the superior loop 28 of the lens may now be understood.

During the implantation procedure, after the inferior loop 26 has been moved into position behind the iris 52, it is necessary to exert downward pressure on the superior loop 28 in order to compress the inferior loop 26 as described previously. The notch 30, which is visible in FIGS. 1-3, allows the surgeon to conveniently engage the superior loop 28 with a hook in order to exert the necessary pressure thereon. The notch 30 is preferably provided in the form of a sharp U-shaped or V-shaped bend formed in the superior loop 28 between the secured and free ends thereof, and lying in the same plane as the remaining portion of the superior loop 28. In the illustrated embodiment, the notch 30 is located at a point approximately three-quarters of the distance from the secured end of the loop 28 to the free end of the loop. Since it is desired to exert pressure on the superior loop 28 in the direction of the lens body 20 and inferior loop 26, the notch 30 is formed so that it points in this direction. Therefore, in FIGS. 1-3, it will be observed that the notch 30 points downward (i.e., toward the 6 o'clock position) in the direction of the lens body 20 and inferior loop 26.

Referring again to FIG. 6, the implantation procedure results in the lens body 20 occupying a central position within the posterior chamber as a result of the counterbalancing radial forces exerted by the inferior and superior loops 26 and 28, which are slightly compressed. Due to the anterior tilt of the loops 26 and 28, posterior or rearward pressure is also exerted on the lens body 20 so that the edge of the flange 32 is urged into contact with the posterior capsule 42 as shown. As noted previously, the inferior and superior loops 26 and 28 are preferably provided with an anterior tilt of about 15°, which is somewhat greater than the 10° to 12° anterior tilt that has previously been employed with other types of posterior chamber lenses. The 15° anterior tilt of the loops produces a greater degree of rearward pressure on the lens body 20, thereby insuring firm contact between the edge of the flange 32 and the posterior capsule 42.

The angulated flange 32 of the lens is useful in preventing several post-operative complications that have occurred in the past following posterior chamber lens implantation. As a result of the flange, the rearward pressure exerted by the loops 26 and 28 is concentrated along the narrow line of contact which exists between the edge of the flange and the posterior capsule 42. This causes a tenting or stretching of the posterior capsule as a whole. The posterior capsule, and particularly the central region of the posterior capsule beneath the lens optic 22, is thereby made smooth and substantially free of wrinkles. As pointed out earlier, post-operative wrinkling of the posterior capsule is believed to be responsible for the double and triple ghost images that some patients experience after receiving posterior chamber lens implants. It is anticipated that the present invention will substantially avoid this result by eliminating or at least minimizing wrinkle formation in the central posterior capsule.

The reason for the enhanced smoothing effect of the flange 32 on the central posterior capsule, as distinguished from the marginal area of the posterior capsule outside the flange, may be explained as follows. The overall amount of stretching of the posterior capsule 42 is, of course, a function of the rearward pressure exerted by the flange 32, and this will be relatively uniform across the entire posterior capsule. The smoothing effect, however, requires not only stretching but also elimination of the wrinkling that may occur even in the stretched condition of the posterior capsule. In particular, radial wrinkles may appear in the marginal area of the posterior capsule since this area of the capsule is supported somewhat unevenly by the zonular ligaments 55. The support of the marginal area of the capsule will be particularly uneven if, as sometimes happens, some of the zonules have been broken during the ECCE procedure. By contrast, the flange 32 provides uniform 360° support for the central area of the posterior capsule. As a result, any of the wrinkles originating at the zonules will be confined to the marginal region of the posterior capsule and will not extend to the central area of the capsule. An analogy may be drawn to an inverted drinking glass with its rim pressed against the center of a stretched sheet of clear thermoplastic film of the "Saran Wrap" type; radial wrinkles may appear between the edge of the sheet and the rim of the glass, but the central portion of the sheet under the glass will be maintained smooth and drum-like by the pressure of the rim ("Saran Wrap" is a trademark of The Dow Chemical Company). The flange 32 functions similarly in the present invention. That is, in addition to causing stretching or tenting of the posterior capsule 42 as a whole, the flange 32 serves as a barrier to wrinkle formation in the central posterior capsule by providing continuous circumferential support for that area of the posterior capsule.

Figure 7:
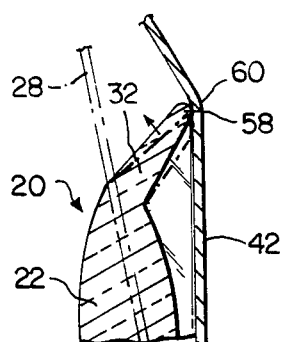
FIG. 7 is a detailed view of a portion of FIG. 6, illustrating the manner in which the circumferential flange of the lens may be made flexible to exert a further stretching effect on the central posterior capsule.

In a particularly preferred embodiment of the present invention, illustrated in FIG. 7, the flange 32 is adapted to flex or deform slightly relative to the lens optic 20 as the flange is urged into contact with the posterior capsule 42 by the resilient loops 26 and 28. The flexing of the flange 32 occurs in a generally radial direction away from the central axis 24 of the lens optic, thereby exerting a further stretching and smoothing effect which is concentrated on the central posterior capsule. This effect is illustrated by the phantom and solid line positions of the flange 32 in FIG. 7. The phantom line position is the position occupied by the flange prior to implantation, that is, in the absence of contact with the posterior capsule 42. The solid line position of the flange illustrates the flexing or deformation of the flange which occurs when it is urged into contact with the posterior capsule 42 as a result of the rearward pressure exerted by the supporting loops 26 and 28. Due to the outward angulation of the flange with respect to the central axis of the lens, it is readily seen that the flexing or deformation of the flange occurs in a radially outward direction, that is, away from the lens axis and toward the marginal or peripheral region of the posterior capsule 42. Of course, since the flange 32 is formed around the entire circumference of the lens optic 22, such flexing or deformation of the flange will occur along the entire 360° zone of contact between the flange and the posterior capsule 42. There will be some degree of frictional adhesion between the edge of the flange 32 and the surface of the posterior capsule 42, and consequently, the outward flexing of the flange 32 will exert an outward radial pull on the central posterior capsule resulting in the desired stretching and smoothing effect.

The flange 32 is preferably tapered in cross section, as shown, having its maximum thickness where it adjoins the lens optic 22 and its minimum thickness at the outer edge which is brought into contact with the posterior capsule 42. This insures that the flexing or deformation of the flange 32 will be most pronounced in the region where it contacts the posterior capsule. The degree of flexing of the flange 32 will depend upon the material of which the lens body 20 is made, and also upon the thickness of the flange, and it will generally be possible to select these factors to produce the desired amount of flexing. The amount of the anterior tilt of the resilient supporting loops 26 and 28 can also be adjusted to produce a greater or lesser degree of rearward pressure on the lens body 20, and hence a greater or lesser degree of flexing of the peripheral flange 32. The flange 32 may be made as thin as necessary to produce the desired amount of flexing relative to the lens optic, although care should be taken not to make the flange thin enough to create a knife edge that might tear the posterior capsule. This possibility can be minimized by providing the flange 32 with a smooth rounded edge 58 as shown in the drawings.

It is preferred to form the flange 32 integrally with the lens optic 22, as illustrated, using the same optical material that is used for the lens optic. However, it is within the scope of the invention to provide the flange 32 as a separate structure which is mechanically attached to the lens optic 22 during the fabrication process. Thus, for example, in situations where the material of the lens optic 22 is too rigid to allow the desired amount of flexibility in the flange 32, the flange may be formed separately using a more resilient material. It should be noted that the flange 32, by virtue of its angulation and peripheral location, does not obstruct the optical portion 22 of the lens body 20, and hence the optical qualities of the material used for the flange are unimportant.

From FIGS. 6 and 7, it can be seen that the flange 32 produces a vaulting of the lens body 20 with respect to the posterior capsule 42, resulting in a space b between the rear face of the lens optic 22 and the posterior capsular surface. In the event of post-operative clouding of the posterior capsule due to epithelial cell migration or some other cause, the space b allows a pulsed YAG laser to be focussed in the vicinity of the posterior capsule 42 without the risk of pitting or crackling of the lens surface. Therefore, a laser capsulotomy procedure can be safely carried out on the posterior capsule 42 without the risk of damage to the lens optic 22. The capsule stretching and smoothing effect of the flange 32, described earlier, also contributes to the safety of this procedure since the possibility that loose folds or wrinkles in the central posterior capsule might touch the rear surface of the lens optic is minimized. It should also be noted that, unlike previously available lens designs in which a simple annular ridge or lip projects perpendicularly from the rear face of the lens, the flange 32 of the present invention extends well beyond the edge of the optical portion 22 of the lens body 20. The clearance between the rear face of the lens and the posterior capsule 42 therefore extends across the entire diameter of the lens body 20, allowing the YAG laser to be focussed virtually anywhere behind the lens without the risk of damage to the implant. The circumferential positioning of the flange 32 also permits the surgeon to better visualize the peripheral retina through the implant, so that pathology in that area can be more easily discovered by visual examination.

The peripheral flange 32 also functions as a barrier for retarding or perhaps even eliminating epithelial cell migration toward the central portion of the posterior capsule. The rearward force exerted by the resilient supporting loops 26 and 28 is concentrated along the narrow line of contact between the edge of the flange 32 and the posterior capsular surface, resulting in an effective magnification of this force in a narrow annular zone surrounding the central posterior capsule. This creates an effective barrier between the peripheral and central regions of the posterior capsule 42. The barrier effect is enhanced by the increased angular tilt of the resilient supporting loops 26 and 28, which increases the amount of rearward pressure exerted on the lens body 20 and flange 32. The barrier effect is also enhanced by the sharp circular bend or crease 60 which is formed in the posterior capsule 42 by the pressure of the flange 32. The reason for this is that the posterior capsule wraps slightly around the edge of the flange 32 in the area of the bend or crease 60, resulting in a larger contact area and hence a larger barrier zone between the flange and the capsule.

In embodiments where the flange is adapted to be flexible, a further enhancement of the barrier effect may be obtained. In these instances, it is expected that the outward flexing of the flange, in addition to causing stretching and smoothing of the central posterior capsule 42, will produce a tighter junctional engagement between the capsular membrane and the edge of the flange 32. Also, since the flexing of the flange 32 will cause it to lie slightly more flatly against the posterior capsule 42, there is a slight broadening of the contact area between the flange and the posterior capsule and hence an increase in the size of barrier zone. It is theorized that these factors will create an enhanced barrier to central migration of epithelial cells or lens fibers, supplementing the barrier effect arising from the simple pressure of the flange 32 against the posterior capsule.

It should be noted that the placement of the flange 32 at the very edge of the lens optic 22, coupled with the outward angulation of the flange, locates the epithelial cell migration barrier relatively far out to the margin of the posterior capsule 42. In contrast, prior art lens designs incorporating a simple annular ridge or lip extending perpendicularly from the rear face of the lens resulted in the barrier being located approximately at the edge of the optic. Therefore, for an optic of a given size, a larger area of the central posterior capsule is protected from epithelial cell migration with the present invention than would be possible using the prior art approach.

It is conceivable that the notches 34 and 36 may adversely affect the barrier function of the flange 32 since they create small gaps along the outermost edge 58 of the flange. This result may be avoided by extending or building up the edges of each notch rearwardly (i.e., in the direction parallel to the lens axis 24) so that they extend as far posteriorly as the edge 58 of the flange. The edge 58 would therefore have crescent-shaped radial indentations at the locations of the notches 34 and 36, rather than complete gaps. Alternatively, the notches 34 and 36 may simply be eliminated and replaced with round positioning holes similar to the hole 38.

A further advantage of the present invention, most clearly evident in FIG. 6, lies in the fact that the angulation of the flange 32 allows it to be placed between the anterior capsule flap 44 and the posterior capsule 42 in situations where the opening 40 in the anterior capsule is smaller than the lens diameter. This insures 360° separation of the anterior capsule flap 44 from the posterior capsule 42 after the lens has been implanted. As a result, the possibility of adhesion between portions of the anterior capsule flap 44 and the posterior capsule 42, which can result in fibrosis and contraction of the posterior capsule, is largely eliminated. This result is not obtainable with prior art barrier lens designs employing a simple annular ridge or lip extending directly rearward from the rear face of the lens.

Figure 8:
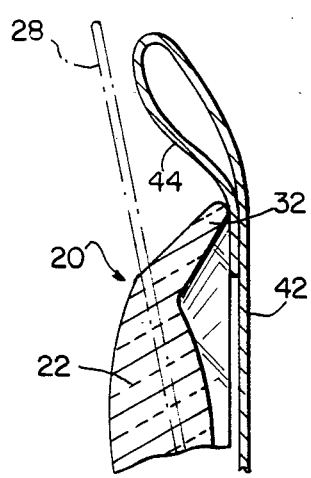
FIG. 8 illustrates an alternative implantation technique in which a capsular seal is produced.

In some cases the surgeon may find it necessary (i.e., due to an insufficiently large opening in the anterior capsule) to implant the lens in a manner such that the peripheral flange 32 is in contact with the anterior capsule flap 44 rather than with the posterior capsule 42 directly. In these situations, a so-called "capsular seal" is created when the anterior capsule flap 44 becomes adherent to the surface of the posterior capsule 42 postoperatively. This phenomenon is illustrated in FIG. 8. The lens implant of the present invention is particularly useful in this situation since the concentration of rearward pressure at the edge of the flange 32 presses the anterior capsule flap 44 firmly into contact with the posterior capsule 42, thereby promoting the formation of the capsular seal. The angulation of the flange 32 is also advantageous in this situation since it causes the capsular seal to be formed relatively far out to the margin of the posterior capsule 42. This reduces the possibility that fibrosis may induce wrinkling of the central posterior capsule.

The lens body 22 and flange 32 are preferably made from clinical quality polymethyl methacrylate (PMMA) or silicone. If desired, ultraviolet filtering can be enhanced by making the lens from a special UV-absorbing polymer such as UV400 ("UV400" is a registered trademark of Optical Radiation Corporation). The material used for the loops 26 and 28 may consist of clinical quality PMMA or polypropylene, and may either be clear or tinted. The loops may be attached to the lens body 20 by any conventional technique. Typically, this is done by drilling holes at spaced points along the edge of the lens body, and then fusing the loops to the lens by thermal or mechanical techniques. It is generally preferred to avoid the use of adhesives in attaching the loops. The lens body 20 may be formed by lathe cutting, injection molding, or spin-cast molding, followed by precision polishing. At the present time, injection molding apprears to be the preferred method for making the lens body, in part because of the difficulty involved in forming the flange 32 by lathe cutting.

Preferred diameters for the optical portion 22 of the lens body 20 are 5.5 millimeters, 6.0 millimeters or 6.5 millimeters. The flange 32 will typically add approximately 0.6 millimeters to the radius of the lens. Therefore, for the optic sizes given previously, the total diameter of the lens body 22 will be 6.7 millimeters, 7.2 millimeters or 7.7 millimeters, respectively. Any desired number of positioning fenestrations can be provided in the lens body, in the form of holes, notches, or a combination of both. These fenestrations are preferably formed in the flange 32 rather than in the lens optic 22, as discussed earlier. If a total of three fenestrations are desired, these may be provided in the pattern shown in FIG. 2. This pattern consists of a 0.4-millimeter diameter round hole at the one o'clock position, together with two 0.4-millimeter diameter edge notches at the four and seven o'clock positions (the clock positions are expressed with respect to the anterior view of the lens as illustrated in FIG. 2, with the twelve o'clock position located at the uppermost edge of the lens). If two fenestrations are desired, these may be provided as a 0.4-millimeter diameter round hole at the one o'clock position and a single 0.4-millimeter diameter edge notch at the seven o'clock position. If a total of four fenestrations are desired, these may be provided by a 0.4-millimeter diameter round hole at the one o'clock position, as before, together with 0.4-millimeter diameter edge notches at the four, seven, and ten o'clock positions. If desired, all of the fenestrations can be provided in the form of 0.4-millimeter round holes, without any notches. Alternatively, all of the fenestrations can be 0.4-millimeter notches rather than round holes. It may also be desirable to form some or all of the holes and/or notches with a 0.3-millimeter diameter, rather than a 0.4-millimeter diameter as indicated previously.

Figure 9:
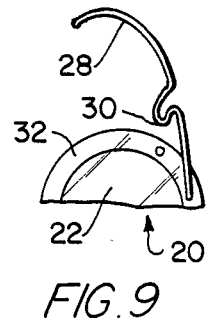
FIGS. 9-11 illustrate three alternative positions for the notch formed in the superior loop of the lens.
Figure 10:
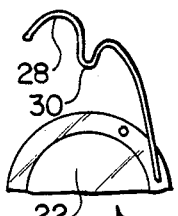
Figure 11:
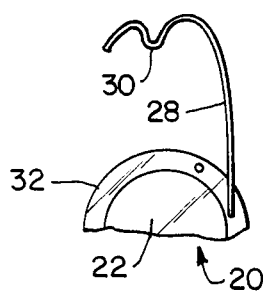

The inferior and superior loops 26 and 28 are preferably 14 millimeters in length, although 13.5-millimeter loops can be used if desired. The thickness of the loops may be 0.14 millimeter, 0.15 millimeter, 0.16 millimeter, or 0.17 millimeter. The notch 30 may be formed in the superior loop 28 at a position approximately three-quarters of the distance from the secured end of the loop to the free end thereof, as illustrated in FIGS. 1-3. However, other positions for the notch 30 may be desirable in some cases. In FIG. 9, for example, the notch 30 is located at a point approximately one-third of the distance from the secured end of the loop 28 to the free end of the loop. In FIG. 10, the notch 30 is located at a point approximately one-half of the distance from the secured end of the loop 28 to the free end of the loop. Finally, in FIG. 11, the notch 30 is located at a point approximately two-thirds of the distance from the secured end of the loop 28 to the free end of the loop. It should be noted that, regardless of the position of the notch 30 along the length of the superior loop 28, the notch 30 should point directly downward (i.e., toward the six o'clock position) in the direction of the lens body 20 as discussed earlier. It will be observed that the notches 30 in the alternative embodiments of FIGS. 9–11 are each shaped to point in this direction.

The supporting loops 26 and 28 may be formed in any one of the conventional shapes. In the principal embodiment, a modified "J" shape is employed for the loops 26 and 28 as best seen in FIGS. 2 and 3. In a modified embodiment, illustrated in FIG. 12, broad curved "J" loops are employed. A further modified embodiment illustrated in FIG. 13, includes loops 66 and 68 in the standard "J" shape. More than two loops may be employed, if desired. Thus, for example, FIG. 14 illustrates an embodiment in which three broad curved "J" loops 70–74 are secured at evenly spaced points around the edge of the lens body. Any of the loops 62–74 of FIGS. 12–14 may be provided with notches, if desired, similar to the notch 30 shown in the preceding Figures.

Referring to FIG. 5, the length d of the flange 32 is preferably between 1.0 millimeter and 3.0 millimeters. The angle a formed by the flange 32 with respect to the central axis 24 of the lens body is preferably in the range between 30° and 38° as mentioned previously. In the preferred embodiment, the flange is approximately 1.1 millimeters in length and defines an angle of about 34° with respect to the lens axis 24. In this embodiment, the flange 32 increases the total radius of the lens 20 by about 0.6 millimeter as already noted. The increased radius attributable to the flange 32 is indicated at e in FIG. 5. The spacing b between the rear face of the lens optic 22 and the rearmost extent of the flange 32 is preferably in the range between 0.25 millimeter and 0.33 millimeter. This corresponds to the spacing between the rear face of the lens and the posterior capsule 42 after the lens has been implanted in the posterior chamber, as illustrated in FIG. 6.

FIGS. 15 and 16 illustrate alternative cross-sectional shapes for the lens optic 22. In FIG. 15, the lens optic 22' has a plano-convex shape, with the plane surface being provided on the front or anterior face of the optic. In FIG. 16, the lens optic 22" has a convex-plano shape, with the plane surface being provided on the rear or posterior face of the optic. In both of these alternative embodiments, the circumferential flange 32 extends posteriorly and radially outward from the edge of the lens optic at an oblique angle with respect to the lens axis, as in the principal embodiment.

The dimension b in FIG. 5 will vary with the power of the lens optic in biconvex and plano-convex embodiments. However, a minimum value of about 0.25 millimeter is preferred for this dimension in order to allow a laser capsulotomy to be performed on the posterior capsule 42 without the risk of damage to the lens. For higher power biconvex and plano-convex lenses, a greater flange length d may be employed to preserve the minimum desired dimension of 0.25 millimeter for the gap b.

It should be pointed out that the gap b of FIG. 5, although advantageous, is not absolutely essential to the present invention and may be omitted in biconvex and plano-convex embodiments. The gap b may be dispensed with, for example, in situations where the ability to perform a laser capsulotomy behind the lens 20 is not considered to be critical. In these instances, the rear face of the lens optic 22 may extend as far posteriorly as the edge 58 of the flange 32. Even in these situations, however, the functions of the flange 32 in stretching and smoothing the central posterior capsule, and in providing a barrier to central migration of epithelial cells, will be preserved as long as the edge 58 of the flange is brought into contact with the posterior capsule 42.

In the embodiments of FIGS. 1-16, the lens body 20 is characterized essentially by a circular inner optic 22 surrounded by a circular outer flange 32, the latter serving as part of the haptic or supporting structure of the lens. FIG. 17 illustrates a modified embodiment in which the circular lens optic 22 is surrounded by a non-circular haptic rim 76, the latter carrying a circumferential flange which is also non-circular but is otherwise similar to that employed in the previous embodiments. The outer haptic rim 76 is narrower in one of its two transverse dimensions than in the other, in order to facilitate insertion of the lens into the eye through a smaller corneal incision than would otherwise be necessary. The haptic rim 76 is preferably in the shape of an ellipse having a major axis 78 and minor axis 80. The resilient supporting loops 26 and 28 are secured to the lens body at diametrically opposed locations in proximity to the end points of the minor axis 80.

Although the invention has been described with reference to particular preferred embodiments, it should be understood that the invention is not limited to the details thereof. To the extent that specific dimensions, materials and methods of manufacture are given, these are intended merely by way of example and not by way of limitation, except where otherwise stated. Various substitutions and modifications have been suggested in the foregoing description, and others will occur to those of ordinary skill in the art. All such substitutions and modifications are intended to be embraced within the scope of the invention as defined in the appended claims.

What is claimed is:

1. An intraocular lens for implantation in the posterior chamber of a human eye following extracapsular cataract extraction, comprising:
    (a) a lens body comprising an inner lens optic having a central axis, and an outer circumferential flange extending posteriorly and radially outward from the edge of said lens optic at an oblique angle with respect to the central axis of the lens optic, said flange extending substantially completely around the circumference of the lens optic and having a substantially uniform length at all points along the circumference of the lens optic; and
    (b) resilient means for supporting the lens body within the posterior chamber of the eye, and for exerting posterior pressure on the lens body to urge the outermost edge of said circumferential flange into substantially 360° contact with the posterior capsule.

2. An intraocular lens as claimed in claim 1, wherein said circumferential flange is integral with the lens optic.

3. An intraocular lens as claimed in claim 1, wherein said circumferential flange extends posteriorly from the lens optic by a sufficient distance to create a space between the rear face of the lens optic and the posterior capsule.

4. An intraocular lens as claimed in claim 3, wherein the distance between the rear face of the lens optic and the posterior capsule is at least 0.25 millimeter.

5. An intraocular lens as claimed in claim 1, wherein said circumferential flange forms an angle of about 30° to 38° with respect to the central axis of the lens optic.

6. An intraocular lens as claimed in claim 1, wherein said lens optic has a biconvex shape.

7. An intraocular lens as claimed in claim 1, wherein said lens optic has a plano-convex shape, with the plane surface being provided on the front face of the lens optic.

8. An intraocular lens as claimed in claim 1, wherein said lens optic has a convex-plano shape, with the plane surface being provided on the rear face of the lens optic.

9. An intraocular lens as claimed in claim 1, wherein said circumferential flange is adapted to flex or deform as it is urged into contact with the posterior capsule by the resilient means, said flexing or deformation occurring in a generally radial direction away from the central axis of the lens optic.

10. An intraocular lens as claimed in claim 9, wherein said circumferential flange is made of the same material as the lens optic, and wherein the flange has a thickness sufficiently less than that of the lens optic to allow the flange to flex or deform relative to the lens optic.

11. An intraocular lens as claimed in claim 10, wherein said circumferential flange is tapered in cross-section, said flange having its maximum thickness where it adjoins the lens optic and having its minimum thickness at the outermost edge which is brought into contact with the posterior capsule.

12. An intraocular lens as claimed in claim 11, wherein the outermost edge of the flange is a smooth rounded edge.

13. An intraocular lens as claimed in claim 10, wherein said material is selected from the group consisting of polymethyl methacrylate and silicone.

14. An intraocular lens as claimed in claim 1, wherein said resilient means comprises at least two curved strands of resilient material extending outwardly from the lens body at spaced points thereon, each of said strands having one end secured to the lens body and the other end free.

15. An intraocular lens as claimed in claim 14, wherein said curved strands lie in planes that are inclined anteriorly with respect to a reference plane lying normal to the central axis of the lens optic.

16. An intraocular lens as claimed in claim 15, wherein the planes containing said curved strands each form an angle of at least 10° with respect to said reference plane.

17. An intraocular lens as claimed in claim 15, wherein the planes containing said curved strands each form an angle of about 15° with respect to said reference plane.

18. An intraocular lens as claimed in claim 1, wherein said lens optic is circular in shape and said flange is carried by an outer haptic rim which is non-circular in shape, said haptic rim being narrower in one of two transverse dimensions than in the other to facilitate insertion of the lens body into the eye through a corneal incision.

19. An intraocular lens as claimed in claim 18, wherein said outer haptic rim is in the shape of an ellipse having a major axis and a minor axis.

20. An intraocular lens as claimed in claim 19, wherein said resilient means comprises first and second curved strands of resilient material extending outwardly from the lens body, each of said strands having one end secured to the lens body and the other end free, said first and second strands having their secured ends positioned at diametrically opposed locations of the lens body in proximity to the end points of the minor axis of the elliptical haptic rim.

21. An intraocular lens for implantation in the posterior chamber of a human eye following extracapsular cataract extraction, comprising:
  a lens body comprising an inner lens optic having a central axis, and an outer circumferential flange extending posteriorly and radially outward from the edge of said lens optic at an oblique angle with respect to the central axis of the lens optic; and
  resilient means for supporting the lens body within the posterior chamber of the eye, and for exerting posterior pressure on the lens body to urge said circumferential flange into contact with the posterior capsule;
  said circumferential flange being adapted to flex or deform as it is urged into contact with the posterior capsule by the resilient supporting means, said flexing or deformation occurring in a generally radial direction away from the central axis of the lens optic.

22. An intraocular lens as claimed in claim 21, wherein said circumferential flange is made of the same material as the lens optic, and wherein the flange has a thickness sufficiently less than that of the lens optic to allow the flange to flex or deform relative to the lens optic.

23. An intraocular lens as claimed in claim 22, wherein said circumferential flange is tapered in cross-section, said flange having its maximum thickness where it adjoins the lens optic and having its minimum thickness at the outermost edge which is brought into contact with the posterior capsule.

24. An intraocular lens as claimed in claim 23, wherein the outermost edge of the flange is a smooth rounded edge.

25. An intraocular lens as claimed in claim 22, wherein said material is selected from the group consisting of polymethyl methacrylate and silicone.

* * * * *